(12) United States Patent
Pincus et al.

(10) Patent No.: US 9,115,213 B2
(45) Date of Patent: Aug. 25, 2015

(54) PHENOTYPIC REVERSION OF PANCREATIC CARCINOMA CELLS

(71) Applicants: Matthew Pincus, Brooklyn, NY (US); Josef Michl, Little Neck, NY (US)

(72) Inventors: Matthew Pincus, Brooklyn, NY (US); Josef Michl, Little Neck, NY (US)

(73) Assignee: The Research Foundation of State University of New York, Albany, NY (US)

( * ) Notice: Subject to any disclaimer, the term of this patent is extended or adjusted under 35 U.S.C. 154(b) by 193 days.

(21) Appl. No.: 13/677,876

(22) Filed: Nov. 15, 2012

(65) Prior Publication Data

US 2013/0065953 A1    Mar. 14, 2013

Related U.S. Application Data

(60) Division of application No. 12/488,209, filed on Jun. 19, 2009, now abandoned, which is a division of application No. 11/825,242, filed on Jul. 5, 2007, now abandoned, which is a continuation of application No. 11/142,051, filed on May 31, 2005, now abandoned.

(60) Provisional application No. 60/575,131, filed on May 28, 2004, provisional application No. 60/575,846, filed on Jun. 1, 2004.

(51) Int. Cl.
*A61K 38/00* (2006.01)
*C07K 14/82* (2006.01)

(52) U.S. Cl.
CPC ............... *C07K 14/82* (2013.01); *A61K 38/00* (2013.01); *C07K 2319/10* (2013.01)

(58) Field of Classification Search
None
See application file for complete search history.

(56) References Cited

U.S. PATENT DOCUMENTS

2006/0258841 A1    11/2006    Michl et al.

OTHER PUBLICATIONS

Johnson et al, Cancer Treatment Reviews, vol. 2 p. 1-31 (1975).*
Burgess et al. (1990) Journal of Cell Biology, 111: 2129-2138.
Lazar et al. (1988) Molecular and Cellular Biology 8(3): 1247-1252.
Schwartz et al. (1987) Proc Nati Acad Sci USA 84: 6408-6411.
Lin et al. (1975) Biochemistry USA 14: 1559-1563.
Kovac et al. (2001) Cancer Chemother, Pharmacol 48: 9-14.
Kanovsky et al (2001) PNAS 98: 12438-12443.
Alder et al. (1996) J. Biol. Chem. 271: 23304-23309.
Derossi et al. (1998) Trends in Cell Biol. 8: 84-87.
Nemunaitis (2003) Biodrugs 17(4): 251-262.

* cited by examiner

*Primary Examiner* — Sheela J Huff
(74) *Attorney, Agent, or Firm* — Dilworth & Barrese, LLP

(57) ABSTRACT

The present invention provides peptides (including analogs and derivatives thereof) corresponding to residues 96-110 and 35-47 of ras-p21, which peptides have attached thereto a membrane-penetrating leader sequence. The subject peptides, analogs and derivatives thereof are useful in treatment of cancers and have been shown to induce phenotypic reversion of pancreatic cancer cells to non-cancerous cells. Pharmaceutical compositions comprising one or more subject peptides are also provided by the present invention. The present invention further provides replication incompetent Adenovirus (AdV) vectors comprising a promoter sequence and a nucleotide sequence encoding a subject peptide. Methods of treating cancer by administering one or more subject peptides, pharmaceutical compositions, and/or AdV vectors are also provided.

3 Claims, 4 Drawing Sheets

```
                        SEQUENCE LISTING

<160> NUMBER OF SEQ ID NOS: 28

<210> SEQ ID NO 1
<211> LENGTH: 14
<212> TYPE: PRT
<213> ORGANISM: Artificial
<220> FEATURE:
<223> OTHER INFORMATION: peptide; amino acid residues 96-110 of
      oncogenic ras-p21 protein

<400> SEQUENCE: 1

Tyr Arg Glu Gln Ile Lys Arg Val Lys Asp Ser Asp Val Pro
1               5                   10

<210> SEQ ID NO 2
<211> LENGTH: 13
<212> TYPE: PRT
<213> ORGANISM: Artificial
<220> FEATURE:
<223> OTHER INFORMATION: peptide: amino acid residues 35-47 of
      oncogenic ras-p21 protein

<400> SEQUENCE: 2

Thr Ile Glu Asp Ser Tyr Arg Lys Gln Val Val Ile Asp
1               5                   10

<210> SEQ ID NO 3
<211> LENGTH: 17
<212> TYPE: PRT
<213> ORGANISM: Artificial
<220> FEATURE:
<223> OTHER INFORMATION: peptide; penetratin leader sequence from
      Antennapedia

<400> SEQUENCE: 3

Lys Lys Trp Lys Met Arg Arg Asn Gln Phe Trp Val Lys Val Gln Arg
1               5                   10                  15

Gly

<210> SEQ ID NO 4
<211> LENGTH: 14
<212> TYPE: PRT
<213> ORGANISM: Artificial
<220> FEATURE:
```

```
<223> OTHER INFORMATION: peptide; HIV-1 TAT membrane penetrating
      sequence

<400> SEQUENCE: 4

Tyr Gly Arg Lys Lys Arg Arg Gln Arg Arg Arg Pro Pro Gln
1               5                   10

<210> SEQ ID NO 5
<211> LENGTH: 13
<212> TYPE: PRT
<213> ORGANISM: Artificial
<220> FEATURE:
<223> OTHER INFORMATION: peptide; D-TAT membrane penetrating sequence

<400> SEQUENCE: 5

Gly Arg Lys Lys Arg Arg Gln Arg Arg Arg Pro Pro Gln
1               5                   10

<210> SEQ ID NO 6
<211> LENGTH: 13
<212> TYPE: PRT
<213> ORGANISM: Artificial
<220> FEATURE:
<223> OTHER INFORMATION: peptide; R-TAT membrane penetrating leader
      sequence

<400> SEQUENCE: 6

Gly Arg Arg Arg Arg Arg Arg Arg Arg Arg Pro Pro Gln
1               5                   10

<210> SEQ ID NO 7
<211> LENGTH: 7
<212> TYPE: PRT
<213> ORGANISM: Artificial
<220> FEATURE:
<223> OTHER INFORMATION: SV40-NLS membrane penetrating leader sequence

<400> SEQUENCE: 7

Pro Lys Lys Lys Arg Lys Val
1               5

<210> SEQ ID NO 8
<211> LENGTH: 16
<212> TYPE: PRT
<213> ORGANISM: Artificial
<220> FEATURE:
<223> OTHER INFORMATION: peptide; nucleoplasm-NLS membrane penetrating
      leader sequence

<400> SEQUENCE: 8

Lys Arg Pro Ala Ala Ile Lys Lys Ala Gly Gln Ala Lys Lys Lys Lys
1               5                   10                  15

<210> SEQ ID NO 9
<211> LENGTH: 17
<212> TYPE: PRT
<213> ORGANISM: Artificial
<220> FEATURE:
<223> OTHER INFORMATION: peptide; HIV REV membrane penetrating leader
      sequence

<400> SEQUENCE: 9

Thr Arg Gln Ala Arg Arg Asn Arg Arg Arg Arg Trp Arg Glu Arg Gln
1               5                   10                  15

Arg
```

```
<210> SEQ ID NO 10
<211> LENGTH: 15
<212> TYPE: PRT
<213> ORGANISM: Artificial
<220> FEATURE:
<223> OTHER INFORMATION: peptide; FHV coat protein membrane penetrating
      leader sequence

<400> SEQUENCE: 10

Arg Arg Arg Arg Asn Arg Thr Arg Arg Asn Arg Arg Arg Val Arg
1               5                   10                  15

<210> SEQ ID NO 11
<211> LENGTH: 19
<212> TYPE: PRT
<213> ORGANISM: Artificial
<220> FEATURE:
<223> OTHER INFORMATION: peptide; BMV GAG membrane penetrating leader
      sequence

<400> SEQUENCE: 11

Lys Met Thr Arg Ala Gln Arg Arg Ala Ala Ala Arg Arg Asn Arg Trp
1               5                   10                  15

Thr Ala Arg

<210> SEQ ID NO 12
<211> LENGTH: 13
<212> TYPE: PRT
<213> ORGANISM: Artificial
<220> FEATURE:
<223> OTHER INFORMATION: peptide; HTLV-II REX membrane penetrating
      leader sequence

<400> SEQUENCE: 12

Thr Arg Arg Gln Arg Thr Arg Arg Ala Arg Arg Asn Arg
1               5                   10

<210> SEQ ID NO 13
<211> LENGTH: 19
<212> TYPE: PRT
<213> ORGANISM: Artificial
<220> FEATURE:
<223> OTHER INFORMATION: peptide; CCMV GAG membrane penetrating leader
      sequence

<400> SEQUENCE: 13

Lys Leu Thr Arg Ala Gln Arg Arg Ala Ala Ala Arg Lys Asn Lys Arg
1               5                   10                  15

Asn Thr Arg

<210> SEQ ID NO 14
<211> LENGTH: 17
<212> TYPE: PRT
<213> ORGANISM: Artificial
<220> FEATURE:
<223> OTHER INFORMATION: peptide; P22 N membrane penetrating leader
      sequence

<400> SEQUENCE: 14

Asn Ala Lys Thr Arg Arg His Glu Arg Arg Arg Lys Leu Ala Ile Glu
1               5                   10                  15

Arg

<210> SEQ ID NO 15
<211> LENGTH: 22
<212> TYPE: PRT
```

```
<213> ORGANISM: Artificial
<220> FEATURE:
<223> OTHER INFORMATION: peptide; LAMBDA N membrane penetrating leader
      sequence

<400> SEQUENCE: 15

Met Asp Ala Gln Thr Arg Arg Arg Glu Arg Arg Ala Glu Lys Gln Ala
1               5                   10                  15

Gln Trp Lys Ala Ala Asn
            20

<210> SEQ ID NO 16
<211> LENGTH: 18
<212> TYPE: PRT
<213> ORGANISM: Artificial
<220> FEATURE:
<223> OTHER INFORMATION: peptide; Phi N membrane penetrating leader
      sequence

<400> SEQUENCE: 16

Thr Ala Lys Thr Arg Tyr Lys Ala Arg Arg Ala Glu Leu Ile Ala Glu
1               5                   10                  15

Arg Arg

<210> SEQ ID NO 17
<211> LENGTH: 16
<212> TYPE: PRT
<213> ORGANISM: Artificial
<220> FEATURE:
<223> OTHER INFORMATION: peptide; Yeast PRP6 membrane penetrating leader
      sequence

<400> SEQUENCE: 17

Thr Arg Arg Asn Lys Arg Asn Arg Ile Gln Glu Gln Leu Asn Arg Lys
1               5                   10                  15

<210> SEQ ID NO 18
<211> LENGTH: 12
<212> TYPE: PRT
<213> ORGANISM: Artificial
<220> FEATURE:
<223> OTHER INFORMATION: peptide; Human U2AF membrane penetrating leader
      sequence

<400> SEQUENCE: 18

Ser Gln Met Thr Arg Gln Ala Arg Arg Leu Tyr Val
1               5                   10

<210> SEQ ID NO 19
<211> LENGTH: 26
<212> TYPE: PRT
<213> ORGANISM: Artificial
<220> FEATURE:
<223> OTHER INFORMATION: peptide; Human C-FOS membrane penetrating
      leader sequence

<400> SEQUENCE: 19

Lys Arg Arg Ile Arg Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 20
<211> LENGTH: 28
<212> TYPE: PRT
<213> ORGANISM: Artificial
```

-continued

```
<220> FEATURE:
<223> OTHER INFORMATION: peptide; Human C-JUN membrane penetrating
      leader sequence

<400> SEQUENCE: 20

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 21
<211> LENGTH: 22
<212> TYPE: PRT
<213> ORGANISM: Artificial
<220> FEATURE:
<223> OTHER INFORMATION: peptide; Yeast GCN4 membrane penetrating
      leader sequence

<400> SEQUENCE: 21

Lys Arg Ala Arg Asn Thr Glu Ala Ala Arg Arg Ser Arg Ala Arg Lys
1               5                   10                  15

Leu Gln Arg Met Lys Gln
            20

<210> SEQ ID NO 22
<211> LENGTH: 18
<212> TYPE: PRT
<213> ORGANISM: Artificial
<220> FEATURE:
<223> OTHER INFORMATION: peptide; membrane penetrating leader sequence

<400> SEQUENCE: 22

Lys Leu Ala Leu Lys Leu Ala Leu Lys Ala Leu Lys Ala Ala Leu Lys
1               5                   10                  15

Leu Ala

<210> SEQ ID NO 23
<211> LENGTH: 18
<212> TYPE: PRT
<213> ORGANISM: Artificial
<220> FEATURE:
<223> OTHER INFORMATION: peptide; p-vec membrane penetrating leader
      sequence

<400> SEQUENCE: 23

Leu Leu Ile Ile Leu Arg Arg Arg Ile Arg Lys Gln Ala Lys Ala His
1               5                   10                  15

Ser Lys

<210> SEQ ID NO 24
<211> LENGTH: 56
<212> TYPE: DNA
<213> ORGANISM: Artificial
<220> FEATURE:
<223> OTHER INFORMATION: primer; nucleotide sequence encoding PNC-7
      peptide

<400> SEQUENCE: 24
tcgagccacc atggggaccg aggattctta cagaaaacaa gtggttatag attaac      56

<210> SEQ ID NO 25
<211> LENGTH: 59
<212> TYPE: DNA
<213> ORGANISM: Artificial
<220> FEATURE:
```

```
<223> OTHER INFORMATION: primer; nucleotide sequence encoding PNC-7
      peptide

<400> SEQUENCE: 25
cggtggtacc cctggtatct cctaagaatg tcttttgttc accaatatct aattgggcc      59

<210> SEQ ID NO 26
<211> LENGTH: 60
<212> TYPE: DNA
<213> ORGANISM: Artificial
<220> FEATURE:
<223> OTHER INFORMATION: primer; nucleotide sequence encoding PNC-2
      peptide

<400> SEQUENCE: 26
cgccgccatg ggctacaggg agcagatcaa gagggtgaag gacagcgacg acgtgccta     60

<210> SEQ ID NO 27
<211> LENGTH: 8
<212> TYPE: PRT
<213> ORGANISM: Artificial
<220> FEATURE:
<223> OTHER INFORMATION: peptide; Arg(8) membrane penetrating leader
      sequence

<400> SEQUENCE: 27

Arg Arg Arg Arg Arg Arg Arg Arg
1               5

<210> SEQ ID NO 28
<211> LENGTH: 13
<212> TYPE: PRT
<213> ORGANISM: Artificial
<220> FEATURE:
<223> OTHER INFORMATION: peptide; X13 sequence from mammalian cytochrome
      P450

<400> SEQUENCE: 28

Met Pro Phe Ser Thr Gly Lys Arg Ile Met Leu Gly Glu
1               5                   10
```

PHENOTYPIC REVERSION OF PANCREATIC CARCINOMA CELLS

CROSS REFERENCE TO RELATED APPLICATIONS

This application is a divisional application of U.S. Ser. No. 12/488,209, filed Jun. 19, 2009; which is a divisional of U.S. Ser. No. 11/825,242, filed Jul. 5, 2007; which is a continuation application of U.S. Ser. No. 11/142,051, filed May 31, 2005, which claims the benefit of U.S. Provisional Application Ser. No. 60/575,131, filed May 28, 2004, and U.S. Provisional Application Ser. No. 60/575,846, filed Jun. 1, 2004, both of which are incorporated by reference herein.

STATEMENT REGARDING FEDERALLY FUNDED RESEARCH

The present invention was funded in part by NIH Grant RO1 CA 42500; the government may have certain rights in the invention.

BACKGROUND OF THE INVENTION

Oncogenic ras-p21 protein, but not its wild-type counterpart protein, induces malignant transformation of mammalian cell lines such as NIH 3T3 cells (1) and has been implicated as a major causative factor in a high proportion of human solid tissue tumors (2). In *Xenopus laevis* oocytes, microinjection of oncogenic (containing Val in place of Gly 12), but not wild-type, p21 induces oocyte maturation (3). Insulin induces oocyte maturation and requires activation of normal cellular ras-p21 (4).

Several agents that strongly block Val 12-p21-induced oocyte maturation have virtually no effect on insulin-induced maturation (5). Among these agents are specific peptides, identified from molecular modeling studies, that correspond to effector domains from both ras-p21 itself, such as the 35-47, 96-110 and 115-126 sequences (5) and from some of its target proteins such as the ras-binding domain of raf (residues 97-110) (6-8) and the SOS guanine nucleotide exchange protein (residues 994-1004) (9, 10). These peptide domains were identified as those that change conformation in response to the presence of single oncogenic amino acid substitutions at positions 12 or 61 or multiple substitutions at positions 10, 12 and 59 when the computed average structures for these proteins either alone or in complex with target proteins were superimposed on that for the wild-type protein.

The finding that these peptides (in addition to other agents) block oncogenic ras-p21 selectively indicates that the oncogenic protein induces mitogenesis by pathways that may overlap with, but are also distinct from, pathways utilized by the wild-type protein. In studies designed to identify pathway differences, it was found that, in oocytes, oncogenic but not insulin-activated wild-type ras-p21 interacts with the transcriptional activating protein, jun and its kinase, jun kinase (JNK) (11, 12), and requires the presence of protein kinase C (PKC) (13). In these studies, it was determined that the peptide whose sequence corresponds to p21 residues 96-110, called PNC-2, blocks the interaction of Val 12-p21 with JNK (11, 12) in a dose-response curve that superimposes on that for its inhibition of Val 12-p21-induced oocyte maturation (5).

Additionally, the peptide whose sequence corresponds to p21 residues 35-47, called PNC-7, encompasses a domain of the protein implicated in its interacting with multiple targets including raf p74 protein, GTPase activating protein (GAP) and the guanine nucleotide exchange protein, SOS (reviewed in ref. 5). This peptide strongly inhibits c-raf-induced oocyte maturation but has no effect on oocyte maturation induced by an oncogenic mutant raf lacking the ras binding domain (RBD) in its amino terminal regulatory domain (14). Both PNC-2 and 7 appear to act on different steps on the oncogenic ras-p21 signal transduction pathway. For example, PNC-2 but not PNC-7 interferes with Val 12-p21-JNK interaction (11, 12) while PNC-7 but not PNC-2 blocks signal transduction through c-raf (15).

Since various cancers involve expression of Val 12-p21 protein, as well as other oncogenic proteins, it would be useful to be able to inhibit expression of such proteins. For example, pancreatic cancer is a nearly always fatal disease with a median survival time of only 80-90 days for a patient diagnosed with the disease. Pancreatic cancer is one of the more lethal forms of cancer in numbers of patients killed in the U.S. Less than 4% of patients are alive 5 years from the time of diagnosis. The present invention provides peptides and pharmaceutical compositions comprising such peptides which when administered to pancreatic cancer cells, not only inhibit oncogenic Val 12-p21 but actually cause cancerous cells to phenotypically revert to non-cancerous cells. The present invention is therefore useful in treating various types of cancers which express Val 12-p21 protein and/or other oncogenic proteins. Treatment of ras-induced tumors converts malignant masses into benign ones, allowing for the halting of metastatic disease.

SUMMARY OF THE INVENTION

The present invention provides peptides comprising at least about ten contiguous amino acids of the amino acid sequence: YREQIKRVKDSDDVP (SEQ ID NO:1), or an analog or derivative thereof, wherein said peptide, analog, or derivative thereof comprises a membrane-penetrating leader sequence attached thereto. Preferably, a peptide has the sequence set forth in SEQ ID NO:1.

The present invention also provides peptides comprising at least about ten contiguous amino acids of the amino acid sequence: TIEDSYRKQVVID (SEQ ID NO:2) or an analog or derivative thereof wherein said peptide, analog, or derivative thereof comprises a membrane-penetrating leader sequence attached thereto. Preferably, a peptide has the sequence as set forth in SEQ ID NO:2.

The peptides of the present invention, including analogs and derivatives thereof, are useful in treating cancer. Preferably, a peptide, analog or derivative thereof as provided herein has the membrane-penetrating leader sequence located at the carboxy terminal end. In another preferred embodiment, the leader sequence comprises predominantly positively charged amino acid residues. Examples of leader sequences for practicing the present invention include but are not limited to penetratin, $Arg_8$, TAT of HIV1, D-TAT, R-TAT, SV40-NLS, nucleoplasmin-NLS, HIV REV, FHV coat, BMV GAG, HTLV-II (REX), CCMV GAG, P22N, Lambda N, Delta N, yeast PRP6, human U2AF, human C-FOS, human C-JUN, yeast GCN4, or p-vec.

Also provided by the present invention are pharmaceutical compositions comprising at least one of the subject peptides or analogs or derivatives thereof comprising a membrane-penetrating leader sequence admixed with a pharmaceutically acceptable carrier.

The present invention also provides methods of treating a patient suffering from cancer. The method comprises administering to said patient a therapeutically effective amount of at least one subject peptide, analog or derivative thereof comprising a membrane penetrating leader sequence. In another embodiment of the invention, there is provided a method of treating a patient suffering from cancer by administering to said patient a therapeutically effective amount of a subject pharmaceutical composition. Preferably, the cancer to be treated is a ras-induced cancer.

In still another embodiment of the invention, there is provided a replication incompetent Adenovirus (AdV) vector comprising a promoter sequence operably linked to a nucleotide sequence encoding a peptide, wherein the peptide comprises at least about ten contiguous amino acids of the amino acid sequence: YREQIKRVKDSDDVP (SEQ ID NO: 1), or an analog or derivative thereof. A replication incompetent Adenovirus (AdV) vector comprising a promoter sequence operably linked to a nucleotide sequence encoding a peptide, wherein the peptide comprises at least about ten contiguous amino acids of the amino acid sequence: TIEDSYRKQVVID (SEQ ID NO:2), or an analog or derivative thereof is also provided. Preferably, the nucleotide sequence further encodes a leader sequence attached to the sequence set forth in SEQ ID NO: 1, 2, or an analog or derivative thereof.

The present invention also provides a method of treating a patient suffering from cancer by administering to the patient, a therapeutically effective amount of a subject AdV vector. A method of inducing phenotypic reversion of cancerous cells to non-cancerous cells in a subject, by administering to the subject, a therapeutically effective amount of a subject AdV vector is also provided.

DETAILED DESCRIPTION OF THE INVENTION

Figures 1A, 1B, 1C, 1D:
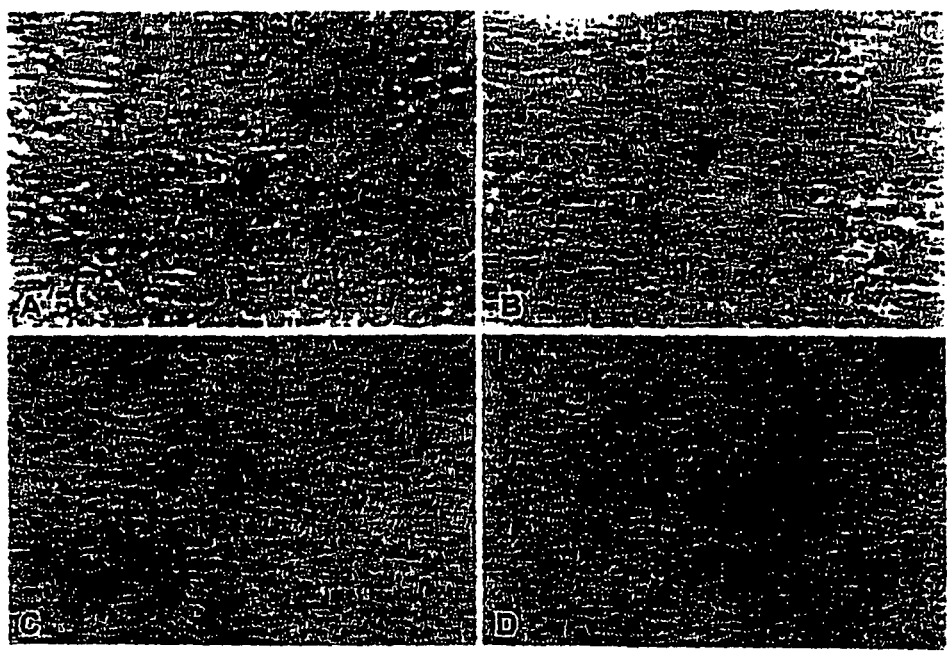
FIG. 1A is a photomicrograph of untreated ras-transformed pancreatic cancer (TUC-3) cells.
FIG. 1B is a photomicrograph of TUC-3 cells treated with X13-leader peptide for two weeks.
FIG. 1C is a photomicrograph of untreated pancreatic acinar (BMRPA1) cells at confluence.
FIG. 1D is a photomicrograph of BMRPA1 cells treated with PNC-2-leader peptide, showing no change in morphology or cell viability.

In accordance with the present invention, it has been surprisingly discovered that peptides designed from molecular modeling studies of the ras-p21 protein induce phenotype reversion of a pancreatic carcinoma cell line but have no effect on normal pancreatic acinar cell growth. The two peptides, designated PNC-2 and PNC-7, block oncogenic ras-induced oocyte maturation but do not block insulin-activated wild type ras-induced maturation.

Since various cancers involve expression of Val 12-p21 protein, inhibition of this protein as well as phenotypic reversion of cancerous cells expressing this protein upon treatment of PNC-2 and/or PNC-7, represents a valuable cancer therapy. One out of every three solid tumors involves expression of Val 12-p21. For example, between 50-75% of colon cancers, greater than 90% of pancreatic cancers, one third of all non-small cell carcinomas of the lung, one fifth of gastric and bladder cancers, as well as many mesotheliomas involve expression of oncogenic ras-p21 protein.

In accordance with the present invention, the peptides PNC-2, PNC-7, analogs and derivatives of such peptides, pharmaceutical preparations and methods of treatment using PNC-2, PNC-7 peptides, analogs, derivatives thereof and pharmaceutical preparations based thereon, are useful in treating a variety cancers. Preferably, the cancers which are treated with the peptides pharmaceutical compositions and methods of the present invention are ras-induced cancers. Treatment of ras-induced tumors by the compositions of the present invention convert malignant masses into benign ones, allowing for the stopping of metastatic disease.

In one aspect of the invention, there is provided a peptide comprising at least about ten contiguous amino acids of the amino acid sequence: YREQIKRVKDSDDVP (SEQ ID NO:1) or an analog or derivative thereof. In a preferred embodiment of the invention, the peptide is designated PNC-2 and comprises the 15 amino acids as set forth in SEQ ID NO:1.

In another aspect of the invention, there is provided a peptide comprising at least about ten contiguous amino acids of the amino acid sequence: TIEDSYRKQVVID (SEQ ID NO:2), or an analog or derivative thereof. In a preferred embodiment of the invention, the peptide is designated PNC-7 and comprises the 13 amino acids as set forth in SEQ ID NO:2.

Preferably, the peptides having the amino acid sequence set forth in SEQ ID NO:1 or SEQ ID NO:2, or an analog or derivative thereof, are fused to a membrane-penetrating leader sequence. In order to be transported across a cell membrane and effect reversion of cancerous cells to normal phenotype, the leader sequence is preferably positioned at the carboxyl terminal end of the peptide, analog, or derivative thereof. Preferably, the leader sequence comprises predominantly positively charged amino acid residues. Examples of leader sequences which may be used in accordance with the present invention include but are not limited to penetratin, $Arg_8$, TAT of HIV1, D-TAT, R-TAT, SV40-NLS, nucleoplasmin-NLS, HIV REV (34-50), FHV coat (35-49), BMV GAG (7-25), HTLV-II REX (4-16), CCMV GAG (7-25), P22N (14-30), Lambda N (1-22), Delta N (12-29), yeast PRP6, human U2AF, human C-FOS (139-164), human C-JUN (252-279), yeast GCN4, and p-vec. Preferably, the leader sequence is the penetratin sequence from antennapedia protein having the amino acid sequence KKWKMRRNQFWVKVQRG (SEQ ID NO:3).

Pharmaceutical compositions comprising at least one of the subject peptides admixed with a pharmaceutically acceptable carrier are also provided. In addition, methods for treating neoplastic disease (cancer) in a subject i.e., inducing phenotypic reversion of cancerous cells to benign cells in a subject suffering from cancer, are provided. In one embodiment, the method comprises administering to the subject, a therapeutically effective amount of a peptide comprising at least about ten contiguous amino acids of the amino acid sequence: YREQIKRVKDSDDVP (SEQ ID NO: 1), or an analog or derivative thereof. Preferably, the peptide or analog or derivative thereof is fused to a membrane-penetrating leader sequence and confers a normal phenotype on cancerous cells. Even more preferably, the membrane-penetrating leader sequence is fused to the carboxy terminal end of the peptide, analog, or derivative thereof. The cancer is preferably a ras-induced cancer.

In another embodiment, the method comprises administering to the subject suffering from cancer, a therapeutically effective amount of a peptide having the sequence set forth in TIEDSYRKQVVID (SEQ ID NO:2), or an analog or derivative thereof. Preferably, the peptide or analog or derivative thereof is fused to a membrane-penetrating leader sequence and confers a normal phenotype on cancerous cells. Even more preferably, the membrane-penetrating leader sequence is fused to the carboxy terminal end of the peptide, analog, or derivative thereof. The cancer is preferably a ras-induced cancer.

In still another embodiment of the invention, the method comprises administering to a subject suffering from cancer, a therapeutically effective amount of a mixture of peptides having the sequence set forth in SEQ ID NO: 1 and SEQ ID NO: 2, or analogs or derivatives thereof. Preferably, the peptides or analogs or derivatives thereof are fused to a membrane-penetrating leader sequence and confer a normal phenotype on cancerous cells. Even more preferably, the membrane-penetrating leader sequence is fused to the carboxy terminal end of the peptides, analogs, or derivatives thereof. The cancer is preferably a ras-induced cancer.

Leader sequences which function to import the peptides of the invention into a cell may be derived from a variety of sources. Preferably, the leader sequence comprises predominantly positively charged amino acid residues since a positively charged leader sequence stabilizes the alpha helix of a subject peptide. Examples of leader sequences which may be linked to the peptides of the present invention are described in Futaki, S. et al (2001) Arginine-Rich Peptides, *J. Biol. Chem.* 276:5836-5840, and include but are not limited to the following membrane-penetrating leader sequences (numbering of the amino acid residues making up the leader sequence of the protein is indicated parenthetically immediately after the name of the protein in many cases):

```
penetratin
                                        (SEQ ID NO: 3)
(KKWKMRRNQFWVKVQRG);

(SEQ ID NO: 27)
(Arg)8 or any poly-R from (R)4-(R)16;

HIV-1 TAT (47-60)
                                        (SEQ ID NO: 4)
(YGRKKRRQRRRPPQ);

D-TAT
                                        (SEQ ID NO: 5)
(GRKKRRQRRRPPQ);

R-TAT
                                        (SEQ ID NO: 6)
G(R)9PPQ;

SV40-NLS
                                        (SEQ ID NO: 7)
(PKKKRKV);

nucleoplasmin-NLS
                                        (SEQ ID NO: 8)
(KRPAAIKKAGQAKKKK);

HIV REV (34-50)-
                                        (SEQ ID NO: 9)
TRQARRNRRRRWRERQR);

FHV (35-49) coat-
                                        (SEQ ID NO: 10)
(RRRRNRTRRNRRRVR);

BMV GAG (7-25)-
                                        (SEQ ID NO: 11)
(KMTRAQRRAAARRNRWTAR);

HTLV-II REX 4-16-
                                        (SEQ ID NO: 12)
(TRRQRTRRARRNR);

CCMV GAG (7-25)-
                                        (SEQ ID NO: 13)
(KLTRAQRRAAARKNKRNTR);

P22 N (14-30)
                                        (SEQ ID NO: 14)
(NAKTRRHERRRKLAIER);

LAMBDA N (1-22)
                                        (SEQ ID NO: 15)
(MDAQTRRRERRAEKQAQWKAAN);

Phi N (12-29)
                                        (SEQ ID NO: 16)
(TAKTRYKARRAELIAERR);

YEAST PRP6 (129-124)
                                        (SEQ ID NO: 17)
(TRRNKRNRIQEQLNRK);

HUMAN U2AF
                                        (SEQ ID NO: 18)
(SQMTRQARRLYV);

HUMAN C-FOS (139-164)
                                        (SEQ ID NO: 19)
KRRIRRERNKMAAAKSRNRRRELTDT;

HUMAN C-JUN (252-279)
                                        (SEQ ID NO: 20)
(RIKAERKRMRNRIAASKSRKRKLERIAR);

YEAST GCN4
                                        (SEQ ID NO: 21)
(KRARNTEAARRSRARKLQRMKQ);

(SEQ ID NO: 22)
KLALKLALKALKAALKLA;

p-vec
                                        (SEQ ID NO: 23)
LLIILRRRIRKQAKAHSK.
```

Other membrane penetrating leader sequences may also be used. Such sequences are widely available and are described e.g., in Scheller et al. (2000) *Eur. J. Biochem.* 267:6043-6049, and Elmquist et al., (2001) *Exp. Cell Res.* 269:237-244.

Preferably, the positively charged leader sequence of the penetratin leader sequence of antennapedia protein is used. This leader sequence has the following amino acid sequence: KKWKMRRNQFWVKVQRG (SEQ ID NO: 3). Preferably, the leader sequence is attached to the carboxyl terminal end of a subject peptide to enable the synthetic peptide to effect phenotypic reversion of cancerous cells.

Structurally related amino acid sequences may be substituted for the disclosed sequences set forth in SEQ ID NOs: 1 or 2 in practicing the present invention. Amino acid insertional derivatives of the peptides of the present invention include amino and/or carboxyl terminal fusions as well as intra-sequence insertions of single or multiple amino acids. Insertional amino acid sequence variants are those in which one or more amino acid residues are introduced into a predetermined site in a subject peptide although random insertion is also possible with suitable screening of the resulting product. Deletional variants may be made by removing one or more amino acids from the sequence of a subject peptide. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
| --- | --- |
| Ala (A) | Ser |
| Arg (R) | Lys |
| Asn (N) | Gln; His |
| Asp (D) | Glu |
| Cys (C) | Ser |
| Gln (Q) | Asn |
| Glu (E) | Asp |
| Gly (G) | Pro |
| His (H) | Asn; Gln |
| Ile (I) | Leu; Val |
| Leu (L) | Ile; Val |
| Lys (K) | Arg; Gln; Glu |
| Met (M) | Leu; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

When the synthetic peptide is derivatised by amino acid substitution, the amino acids are generally replaced by other amino acids having like properties such as hydrophobicity, hydrophilicity, electronegativety, bulky side chains and the like. As used herein, the terms "derivative", "analogue", "fragment", "portion" and "like molecule" refer to a subject peptide having the amino acid sequence as set forth in SEQ ID NOs:1 or 2, having an amino acid substitution, insertion, addition, or deletion, as long as said derivative, analogue, fragment, portion, or like molecule retains the ability to enter and effect phenotypic reversion of cancer cells, while having no effect on normal, non-cancerous cells.

The synthetic peptides of the present invention may be synthesized by a number of known techniques. For example, the peptides may be prepared using the solid-phase technique initially described by Merrifield (1963) in *J. Am. Chem. Soc.* 85:2149-2154. Other peptide synthesis techniques may be found in M. Bodanszky et al. *Peptide Synthesis*, John Wiley and Sons, 2d Ed., (1976) and other references readily available to those skilled in the art. A summary of polypeptide synthesis techniques may be found in J. Sturart and J. S. Young, *Solid Phase Peptide Synthesis*, Pierce Chemical Company, Rockford, Ill., (1984). Peptides may also be synthesized by solution methods as described in *The Proteins*, Vol. II, 3d Ed., Neurath, H. et al., Eds., pp. 105-237, Academic Press, New York, N.Y. (1976). Appropriate protective groups for use in different peptide syntheses are described in the texts listed above as well as in J. F. W. McOmie, *Protective Groups in Organic Chemistry*, Plenum Press, New York, N.Y. (1973). The peptides of the present invention may also be prepared by chemical or enzymatic cleavage from larger portions of the ras-p21 protein or from the full-length ras-p21 protein. Likewise, leader sequences for use in the synthetic peptides of the present invention may be prepared by chemical synthesis or enzymatic cleavage from larger portions or the full-length proteins from which such leader sequences are derived.

Additionally, the peptides of the present invention may also be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular subject peptide. The present invention also contemplates use of a deoxyribonucleic acid (DNA) molecule that defines a gene coding for, i.e., capable of expressing a subject peptide or a chimeric peptide from which a peptide of the present invention may be enzymatically or chemically cleaved.

Consistent with the observed properties of the peptides of the invention, the subject peptides may be used to induce phenotypic reversion of neoplastic or malignant cells, i.e., cancer cells in animals, preferentially humans. The synthetic peptides of the present invention are thus administered in an effective amount to convert malignant cells or masses into benign cells or masses in a subject animal or human. Reversion of cancerous cells or masses into benign cells or masses would have an additional benefit of halting metastasis and the spread of metastatic disease.

The synthetic peptides of the present invention may be administered preferably to a human patient as a pharmaceutical composition containing a therapeutically effective dose of at least one synthetic peptide according to the present invention together with a pharmaceutical acceptable carrier. The term "therapeutically effective amount" or "pharmaceutically effective amount" means the dose needed to produce in an individual, phenotypic reversion of neoplastic or malignant cells, i.e., cancer cells to benign or non-cancerous cells.

Preferably, compositions containing one or more of the synthetic peptides of the present invention are administered intravenously for the purpose of treating neoplastic or malignant disease such as cancer. Examples of different cancers which may be effectively treated using one or more the peptides of the present invention include but are not limited to: breast cancer, prostate cancer, lung cancer, cervical cancer, colon cancer, melanoma, pancreatic cancer and all solid tissue tumors (epithelial cell tumors) and cancers of the blood including but not limited to lymphomas and leukemias. Preferably, the cancer to be treated in accordance with the present invention is a ras-induced cancer such as colon cancer, pancreatic cancer, non-small cell carcinoma of the lung, gastric cancer, bladder cancer and mesotheliomas. Most preferably the cancer to be treated is pancreatic cancer.

Administration of the synthetic peptides of the present invention may be by oral, intravenous, intranasal, suppository, intraperitoneal, intramuscular, intradermal or subcutaneous administration or by infusion or implantation. When administered in such manner, the synthetic peptides of the present invention may be combined with other ingredients, such as carriers and/or adjuvants. There are no limitations on the nature of the other ingredients, except that they must be pharmaceutically acceptable, efficacious for their intended administration, cannot degrade the activity of the active ingredients of the compositions, and cannot impede importation of a subject peptide into a cell. The peptide compositions may also be impregnated into transdermal patches, or contained in subcutaneous inserts, preferably in a liquid or semi-liquid form which patch or insert time-releases therapeutically effective amounts of one or more of the subject synthetic peptides.

The pharmaceutical forms suitable for injection include sterile aqueous solutions or dispersions and sterile powders for the extemporaneous preparation of sterile injectable solutions or dispersions. The ultimate solution form in all cases must be sterile and fluid. Typical carriers include a solvent or dispersion medium containing, e.g., water buffered aqueous solutions, i.e., biocompatible buffers, ethanol, polyols such as glycerol, propylene glycol, polyethylene glycol, suitable mixtures thereof, surfactants or vegetable oils. Sterilization may be accomplished utilizing any art-recognized technique, including but not limited to filtration or addition of antibacterial or antifungal agents. Examples of such agents include paraben, chlorbutanol, phenol, sorbic acid or thimerosal. Isotonic agents such as sugars or sodium chloride may also be incorporated into the subject compositions.

As used herein, a "pharmaceutically acceptable carrier" includes any and all solvents, dispersion media, coatings, antibacterial and antifungal agents, isotonic agents and the like. The use of such media and agents are well known in the art.

Production of sterile injectable solutions containing the subject synthetic peptides is accomplished by incorporating one or more of the subject synthetic peptides described hereinabove in the required amount in the appropriate solvent with one or more of the various ingredients enumerated above, as required, followed by sterilization, preferably filter sterilization. In order to obtain a sterile powder, the above solutions are vacuum-dried or freeze-dried as necessary.

Inert diluents and/or assimilable edible carriers and the like may be part of the pharmaceutical compositions when the peptides are administered orally. The pharmaceutical compositions may be in hard or soft shell gelatin capsules, be compressed into tablets, or may be in an elixir, suspension, syrup or the like.

The subject synthetic peptides are thus compounded for convenient and effective administration in pharmaceutically effective amounts with a suitable pharmaceutically acceptable carrier in a therapeutically effective dosage. Examples of a pharmaceutically effective amount include peptide concentrations in the range from about at least about 25 µg/ml to at least about 300 µg/ml.

A precise therapeutically effective amount of synthetic peptide to be used in the methods of the invention applied to humans cannot be stated due to variations in stage of neoplastic disease, tumor size and aggressiveness, the presence or extent of metastasis, etc. In addition, an individual's weight, gender, and overall health must be considered and will affect dosage. It can be generally stated, however, that the synthetic peptides of the present invention be administered in an amount of at least about 10 mg per dose, more preferably in an amount up to about 1000 mg per dose. Since the peptide compositions of the present invention will eventually be cleared from the bloodstream, re-administration of the pharmaceutical compositions is indicated and preferred.

The synthetic peptides of the present invention may be administered in a manner compatible with the dosage formulation and in such an amount as will be therapeutically effective. Systemic dosages depend on the age, weight, and condition of the patient and the administration route. An exemplary suitable dose for the administration to adult humans ranges from about 0.1 to about 20 mg per kilogram of body weight. Preferably, the dose is from about 0.1 to about 10 mg per kilogram of body weight.

In accordance with the present invention, there is also provided a method of treating neoplastic disease. The method comprises administering to a subject in need of such treatment, a therapeutically effective amount of a synthetic peptide hereinbefore described, including analogs and derivatives thereof. Thus for example, in one embodiment, an effective amount of a peptide comprising at least about ten contiguous amino acids as set forth in SEQ ID NO: 1 or an analog or derivative thereof, fused on its carboxy terminal end to a leader sequence may be administered to a subject. An effective amount of a peptide having the amino acid sequence as set forth in SEQ ID NO:2 or an analog or derivative thereof, fused on its carboxy terminal end to a leader sequence may also be administered to a subject. In accordance with a method of treatment, a mixture of synthetic peptides may be administered. Thus, for example, in addition to administering one of the peptides, or analogs or derivatives thereof hereinbefore described in an effective amount, mixtures of two or more peptides or analogs or derivatives hereinbefore described may be administered to a subject.

In another aspect of the present invention, there are provided expression vehicles comprising replication incompetent Adenovirus (AdV) and having a promoter sequence operably linked to a coding sequence for a subject peptide, e.g., nucleotide sequences encoding those peptides described above i.e., SEQ ID NO: 1, SEQ ID NO: 2, or analogs or derivatives thereof as described fully above. As described above, more than one triplet (codon) can code for a particular amino acid residue. Table 2 shows the different combinations of codons which may be used to encode the amino acid sequence set forth in SEQ ID NO: 1. Table 3 shows the different combinations of codons which may be used to encode the amino acid sequence set forth in SEQ ID NO: 2. The amino acid sequence of SEQ ID NO: 1 I is shown in the top line of Table 2 in bold. The amino acid sequence of SEQ ID NO: 2 is shown in the top line of Table 3 in bold.

TABLE 2

| Y | R | E | Q | I | K | R | V | K | D | S | D | D | V | P |
|---|---|---|---|---|---|---|---|---|---|---|---|---|---|---|
| TAT | AGA | GAA | CAA | ATT | AAG | CGT | GTT | AAG | GAT | TCT | GAT | GAT | GTT | CCU |
| TAC | AGG | GAG | CAG | ATC | AAA | CGC | GTC | AAA | GAC | TCC | GAC | GAC | GTC | CCC |
|   |   |   |   |   |   | CGT |   | ATA |   | CGA | GTA |   |   | TCA | | | GTA CCA |
|   |   |   |   |   |   | CGC |   |   |   | CGG |   |   |   | TCG |   |   | CCG |
|   |   |   |   |   |   | CGA |   |   |   | AGA |   |   |   | AGT |   |   |   |
|   |   |   |   |   |   | CGG |   |   |   | AGG |   |   |   | AGC |   |   |   |

TABLE 3

| T | I | E | D | S | Y | R | K | Q | V | V | I | D |
|---|---|---|---|---|---|---|---|---|---|---|---|---|
| ACT | ATT | GAA | GAT | TCT | TAT | CGT | AAG | CAA | GTT | GTT | ATT | GAT |
| ACC | ATC | GAG | GAC | TCC | TAC | CGC | AAA | CAG | GTC | GTC | ATC | GAC |

TABLE 3 -continued

| T | I | E | D | S | Y | R | K | Q | V | V | I | D |
|---|---|---|---|---|---|---|---|---|---|---|---|---|
| ACA | ATA | | | TCA | | CGA | | | GTA | GTA | ATA | |
| ACG | | | | TCG | | CGG | | | | | | |
| | | | | AGT | | AGA | | | | | | |
| | | | | AGC | | AGG | | | | | | |

With respect to using nucleotide sequences encoding an analog or derivative of the amino acid sequences set forth in SEQ ID NOs: 1 or 2, one skilled in the art can refer to a table of the Genetic Code to select appropriate codons.

A number of different classes of Ad vectors exist, and may be used in the methods of the present invention. Such Ad vectors are described in the literature and are readily available. See refs. 26 and 27. For example, in accordance with the present invention, an Ad vector may be used wherein the E1 and/or E3 genes have been removed, allowing the introduction of up to about 6.5 kb of transgene under the control of a heterologous promoter. See ref. 28. The defective E1 viruses may be propagated in an E1-complementing cell line, such as 293A cells, which cells provided the E1 gene in trans.

Alternatively, an Ad vector may be used which in addition to lacking the E1 and E3 genes, also lack the E2 genes. See e.g., refs. 29 and 30.

In addition, helper-dependent (HD) or gutted vectors deleted of most or all Ad coding sequences may be used in accordance with the present invention. Such vectors have great potential as gene transfer vectors for gene therapy since long term expression of therapeutic genes have been observed in mice as well as monkeys. The production of these gutted vectors in tissue culture requires a complementing helper virus to provide the proteins required for growth and assembly of the gutted vector in trans. See refs. 31-33. The disclosures of these papers and all references cited herein, are incorporated by reference as if fully set forth.

As discussed above, in the present application directed to viral therapy of neoplastic disease, e.g., cancer, where the goal of the therapy is clearance of the target tissue, a host anti-Ad immune response targeting the vector infected cells is considered desirable. Thus, a gutted Ad vector may not be as preferred as some of the earlier generation vectors which elicit a stronger immune response in the host.

An Ad vector may be based on a two-plasmid system, an entry plasmid and a destination vector made from E1 and E3 gene deleted adenoviral genome that contains a promoter operably linked to a nucleotide sequence encoding one of the peptides described above (SEQ ID NOs: 1 or 2) as well as analogs or derivatives thereof. The two-plasmid system is thoroughly described in refs. 28, 34, and 35. The E1 and E3 gene deletions prevent the virus from replicating in cells that do not express E1 and E3 proteins.

For example, the entry plasmid contains the gene encoding a subject peptide which plasmid is cloned into the AdV via a lambda recombination reaction. The replication incompetent vector may be propagated in 293A cells, which are bioengineered human embryonic kidney cells transformed by AdV genomic DNA (Wang et al., 2000). This cell line supplements the deficient genes required for viral replication.

The replication incompetent AdV vectors of the present invention can be constructed using standard recombinant DNA methods. Standard techniques for the construction of vectors are well-known to those of ordinary skill in the art and can be found in references such as Sambrook, Fritsch and Maniatis, 1989, or any of a number of laboratory manuals on recombinant DNA technology that are widely available. A variety of strategies are available for ligating fragments of DNA, the choice of which depends on the nature of the termini of the DNA fragments and can be readily determined by the skilled artisan. There are a number of different promoters which may be operably linked to the nucleotide sequences encoding a subject peptide. The promoter should function in the cells of a subject undergoing viral therapy with a subject AdV vector. There are a number of widely available promoters which may be used in the AdV vectors of the present invention. Examples of such promoters include, but are not limited to: CMV, SV40, RSV, LTR, beta-actin, EF-1 alpha, Gal-E1b, UbC, beta-Casein, EM-7, EF, TEF1, CMV-2 and Bsd. In a preferred embodiment, the promoter is CMV.

The recombinant vectors may then be subsequently rebuilt into intact viruses using standard methods such as that described in ref. 36, which is incorporated by reference herein as if fully set forth. Other references which describe rebuilding recombinant vectors into intact viruses include ref. 37, also incorporated by reference herein as if fully set forth.

Once a subject AdV vector is constructed, it may be used to treat patients suffering from different types of cancer. Therapy of neoplastic disease (cancer) may be accomplished by administering to a patient suffering from such disease a composition comprising the adenovirus vectors of the present invention. A human patient or nonhuman mammal suffering from a carcinoma may be treated by administering an effective antineoplastic dosage of a subject vector. The subject AdV vectors comprising a promoter operably linked to a nucleotide encoding a subject peptide are useful in treating a number of different cancers including but not limited to breast cancer, prostate cancer, lung cancer, cervical cancer, colon cancer, melanoma, pancreatic cancer, all solid tissue tumors (epithelial cell tumors) and cancers of the blood including but not limited to lymphomas and leukemias. In a preferred embodiment, the cancer to be treated is pancreatic cancer.

Suspensions of infectious adenovirus particles may be applied to neoplastic tissue by various routes, including intravenous, intraperitoneal, intramuscular, subdermal, and topical. Other routes include inhalation as a mist (e.g., in treating lung cancer) or direct application such as by swabbing a tumor site, e.g., cervical carcinoma, or during surgery if necessary. An adenovirus suspension may also be administered by infusion, e.g., into the peritoneal cavity for treating ovarian cancer. Other suitable routes include direct injection into a tumor mass, such as a breast tumor, via enema (colon cancer) or catheter in the case of bladder cancer.

The actual dosage may vary from patient to patient based on the age, weight, type and progression of cancer, location of tumor(s), presence of metastases, and overall condition of the patient. It can generally be said, however, that an adenovirus suspension containing about $10^3$ to about $10^{15}$ or more virion particles per ml may be administered. Re-administration of the AdV vector suspension may be performed as necessary.

The AdV vectors of the present invention may be admixed in a sterile composition containing a pharmacologically effective dosage of one or more subject AdV vectors. Generally speaking, the composition will comprise about $10^3$ to about $10^{15}$ or more AdV particles in an aqueous suspension. The sterile composition is usually an aqueous solution such as e.g., water, buffered water, 0.4% saline, 0.3% glycine and the like. Such compositions may contain pharmaceutically acceptable auxiliary substances e.g., to mimic physiological conditions such as pH adjusting and buffering agents, toxicity adjusting agents and the like, e.g., sodium acetate, sodium chloride, potassium chloride, calcium chloride, sodium lactate, etc. The compositions may also comprise excipients that enhance infection of cells by the subject AdV vectors.

The following examples further illustrate the invention, and are not meant in any way to limit the scope thereof.

EXAMPLE I

Materials and Methods

Peptides. Three peptides, attached to the penetratin leader sequence, KKWKMRRNQFWVKVQRG (SEQ ID NO:3), designated as "leader," on their carboxyl terminal ends, were synthesized by solid phase methods: the two ras-p21 peptides corresponding to p21 residues 35-47 (TIEDSYRKQVVID) (SEQ ID NO:2) and 96-110 (YREQIKRVKDSDVP) (SEQ ID NO:1)), denoted as PNC-7 and PNC-2, respectively; and the negative control X13 sequence (from mammalian cytochrome P450) (MPFSTGKRIMLGE) (SEQ ID NO:28). With the penetratin sequence attached to their carboxyl terminal ends, each of these peptides is denoted as PNC-7-leader, PNC-2-leader and X13-leader, respectively. All peptides were purified to >95 percent purity.

Plasmids.

Construction of the plasmids that express the Ha-ras Val 12-p21 peptide sequence 96-110 (PNC2) and the control X13 peptide from mammalian cytochrome p450 has been described (21). The nucleotide sequences for PNC-2 and X13 peptides are given in ref. 21. The nucleotide sequences, including the 5' sticky end, used to encode the PNC-7 peptide were 5'-T CGA GCC ACC ATG GGG ACC GAG GAT TCT TAC AGA AAA CAA GTG GTT ATA GAT TAA C (SEQ ID NO: 24) and 3'-CGG TGG TAC CCC TGG TAT CTC CTA AGA ATG TCT TTT GTT CAC CAA TAT CTA ATT GGG CC (SEQ ID NO:25). Briefly, all of the oligonucleotides (plus and minus strands) encoding each sequence (PNC-2, PNC-7 and X13) and including a Not1(5') and Kpn1(3') restriction site were synthesized by solid phase methods; sequential degradation of each oligonucleotide confirmed its sequence. These oligonucleotides were then incorporated into the pOPRSVI/MCS vector from the Lac switch II isopropylthioglucose (IPTG)-inducible mammalian expression system from Stratagene (LaJolla, Calif.) by cutting this vector with Kpn1 and Not1 and then ligating the oligomers into the plasmid with T4 ligase overnight at 4° C. The vectors containing the cloned oligonucleotides were transfected into DH5á competent cells (Gibco-BRL, Grand Island, N.Y.) and spread on LBamp plates for overnight incubation. Colonies from each plate were selected and grown at 37° C. in 5 ml of LBamp liquid media. DNA was prepared by the Qiagen (Valencia, Calif.) miniprep procedure, cut with Kpn1/Not1, and run on 2 percent agarose/TAE to estimate the size of the inserts. Clones with the correct size DNA inserts were regrown in 500 ml LBamp overnight at 37° C., and plasmids were then purified by the Qiagen maxiprep method. An aliquot of each positive DNA was sequenced using T3 or T7 primers.

We note that, in our former paper describing these plasmids, an error occurred in the 5' nucleotide sequence encoding PNC-2. This sequence should have read:

Cells.

As described in several prior publications (16, 17, 20), we have developed two cell lines, one a normal contact-inhibited line of rat pancreatic acinar cells, called BMRPA1.430 (BMRPA1) cells and the other a pancreatic acinar carcinoma obtained by transfection of BMRPA1 cells with a plasmid containing an activated human K-ras oncogene [single base mutation at codon 12, valine substitution for the wild type glycine in the ras protein (K-ras$^{val12}$); a kind gift of Dr. M. Perucho (CIBR, La Jolla, Calif.)] and a neomycin resistance gene. BMRPA1 cells have an epithelial cell phenotype, form acinar structures in culture, have no c-ki-ras nor p53 mutations, are unable to grow in anchorage-independent conditions and do not form tumors in Nu/Nu mice (17). In addition, they phenotypically maintain differentiated cell functions such as continued enzyme production and activation of zymogen secretion by secretagogue. On the other hand, ras-transformed BMRPA1 or TUC-3 cells, selected after transfection for their basis resistance to G418 and the overexpression of K-ras$^{val12}$, no longer display an epithelial cell phenotype and acinar cell functions; they grow significantly faster than BMRPA1 cells, have a transformed spindle cell phenotype and form colonies under anchorage-independent conditions in vitro and tumors in vivo in nude mice.

Peptide Incubation Experiments.

Approximately 300,000 cells (either BMRPA1 or TUC-3) were plated in each of six wells and were allowed to adhere overnight. In one set of experiments, the initial media consisted of DMEM with 10% fetal bovine serum that contained no peptide. In another set of experiments, the initial media contained peptide. In the first set, media containing peptide was added after 24 hours; in both sets, after the first 24 hours, the media was changed every 24 hours and always contained peptide at a particular concentration. Cells were observed daily for three weeks for changes in morphology and growth characteristics. Peptides were present at concentrations of 1, 10, 50, 100 and 100 ug/ml.

Transfection Experiments.

Approximately 300,000 TUC-3 cells were plated overnight in a six-well dish and were allowed to adhere overnight. To three wells, 5.5 µg of either PNC-2 or PNC-7 plasmid were added and, to the other three wells, 5.6 µg of X13 plasmid were added. To each of these wells, Superfect transfection agent (Qiagen) was added, using the Qiagen protocol, to enhance transfection efficiencies. We found that a 1:2 ratio of plasmid DNA to Superfect reagent gave the highest transfection efficiencies when compared with 1:5 and 1:10 ratios. Treated cells were then plated in selective medium containing 100 µg/ml G418 and 200 ug/ml of ampicillin together with 1 mM isopropylthioglucose (IPTG). The cells were washed and the medium changed every 24 hours. Viable cells were observed for morphology and growth characteristics over a two-week period.

Explantation of Cells into Nude Mice.

To evaluate cells that appeared to be morphologically revertant to the normal phenotype, approximately 5×10$^6$ morphologically revertant TUC-3 cells treated for two weeks with 100 µg/ml of PNC-2 were injected subcutaneously into Upper
(SEQ ID NO: 26)
5'-CGCCGCCATGGGCTACAGGGAGCAGATCAAGAGGGTGAAGGACAGCGACGACGTGCCCTA In our original paper the highlighted C was inadvertently omitted.

the posterior cervical fatpad of each of five Nu/Nu mice. Similarly, 5×10$^6$ untreated TUC-3 cells were explanted into another five Nu/Nu mice. Daily observations, over a 120 day period, were made on both sets of mice to determine if tumor nodules appeared at the site of injection.

EXAMPLE II

Results

Effects of Peptides on TUC-3 and BMRPA1 Cells.

FIGS. 1A and 1C show the morphology of untreated TUC-3 pancreatic carcinoma cells and their normal counterpart BMRPA1 pancreatic acinar cells, respectively. The former are not-contact-inhibited and do not form monolayers but are "heaped up" on one another with considerable pleomorphism between cells and indistinct cell boundaries. The latter form contact-inhibited monolayers with well-defined cell boundaries. Panel B in FIG. 1 shows that incubation of the X13-leader control peptide with TUC-3 cells for two weeks has no effect on their transformed morphologies. As expected, incubation of this control peptide with BMRPA1 cells has no effect (not shown). Incubation of BMRPA1 cells with PNC2-leader peptide likewise has no effect on the morphology of these cells (Panel D in FIG. 1).

Effects of PNC-2-Leader and PNC-7-Leader on TUC-3 Cells.

Figures 2A, 2B, 2C:
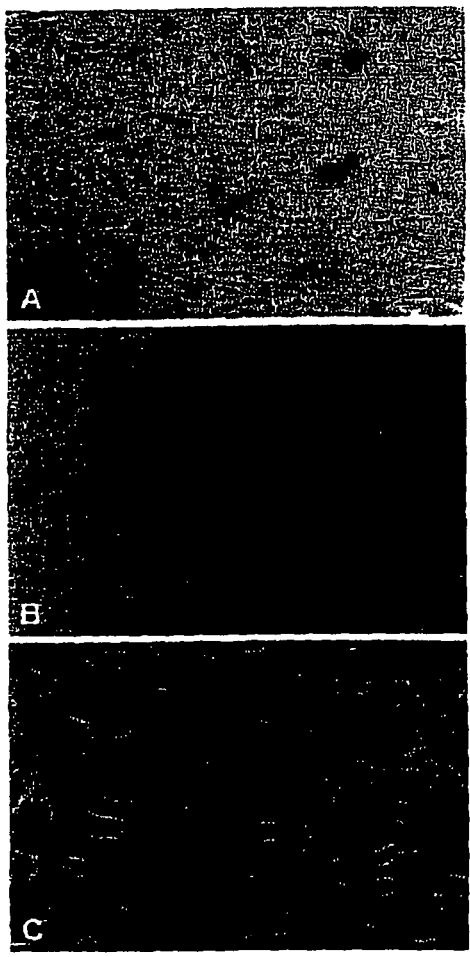
FIG. 2A. is a photomicrograph showing the effects of 100 µg/ml of PNC-2-leader on TUC-3 cells after two weeks of treatment.
FIG. 2B is a photomicrograph showing the effects of 100 µg/ml of PNC-2-leader on TUC-3 cells after one day of treatment. In the center of the figure, a focus of morphologically revertant cells is shown.
FIG. 2C is a photomicrograph showing the effects of 100 µg/ml PNC-7-leader peptide on TUC-3 cells after two weeks of treatment.

Treatment of TUC-3 cells with PNC-2-Leader (100 μg/ml) for 1 week results in a change in cell morphology as shown in FIG. 2A. As can be seen in this figure, the cells appear very similar to BMRPA1 cells (FIG. 1C); the cells grow into contact-inhibited monolayers and show distinct cell boundaries. This effect was achieved at concentrations as low as 1 ug/ml. At this low concentration, complete phenotypic reversion was achieved after two weeks. After one day of treatment, foci of acinar cellular differentiation appear; an example of a focus of revertant cells is shown in FIG. 2B.

Treatment of TUC-3 cells with PNC-7-leader peptide at concentrations of 100 and 200 ug/ml likewise resulted in phenotypic reversion of the cells as shown in FIG. 2C for cells growing into confluence. In contrast to the results obtained with PNC-2-leader peptide, complete reversion after two weeks of incubation of TUC-3 cells with PNC-7-leader was achieved only at concentrations $ 100 ug/ml.

Transfection of TUC-3 Cells with Inducible Plasmids Encoding PNC-2 and X13 Peptides.

Since both PNC-2- and 7-leader peptides induce phenotypic reversion while X13-leader control peptide does not, we conclude that induction of reversion is specific to the two ras-p21 peptides and that the leader sequence, besides enabling membrane penetration, does not contribute to the induction of phenotypic reversion. To test the latter conclusion further, i.e. that PNC-2 and PNC-7 peptides alone, without the leader sequence, can induce phenotypic reversion, we prepared plasmids encoding these and the negative control X13 sequences and transfected them into TUC-3 cells. In a previous publication, we described the preparation of these plasmids which simultaneously confer G418 and ampicillin resistance under the lac promoter (21). We co-microinjected these plasmids with Val 12-p21 protein into *Xenopus laevis* oocytes and found that oocytes injected with either PNC-2 or PNC-7 but not X13 plasmid, in the presence of isopropylthioglucose (IPTG), did not undergo maturation (21). When we transfected each of these plasmids into TUC-3 cells growing in the selective medium, viable cells expressing X13 peptide continued to grow in the presence of IPTG and exhibited the transformed morphology shown in Panel A in FIG. 1.

Figures 3A, 3B, 3C:
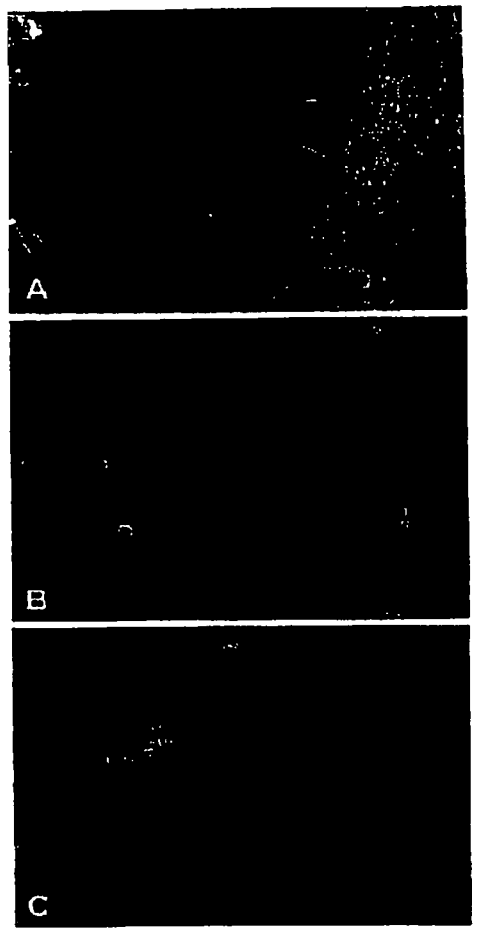
FIG. 3A is a photomicrograph taken one week after plating transfected (with PNC-2-expressing plasmid) viable TUC-3 cells in selective media. Foci of reversion can be observed (left and middle of figure). Remaining transformed cells can be seen on the right side of the figure.
FIG. 3B is a photomicrograph showing that all transfected (with PNC-2-expressing plasmid) TUC-3 cells revert two weeks after transfection and selection of viable cells.
FIG. 3C is a photomicrograph of TUC-3 cells transfected with PNC-7-expressing plasmid, two weeks after transfection, showing cell and nuclear enlargement. These cells grow sluggishly into stable monolayers.

On the other hand, during a period of two weeks post-transfection with PNC-2 plasmid, all viable TUC-3 cells became progressively differentiated as shown in panels A (after 1 week) and B (after 2 weeks) of FIG. 3. As can be seen in panel A of FIG. 3, after one week, many cells adopted the untransformed phenotype (center and left of panel A) while some cells exhibited the transformed phenotype (right side of figure). At the end of two weeks, all cells exhibited the morphology shown in panel B of FIG. 3. As can be seen in this figure, the cells have distinct cell boundaries and exhibit the same morphology as untransformed BMRPA1 cells in growth phase. These cells eventually grew into contact-inhibited monolayers with a morphology that was the same as shown in FIG. 1, panel C.

Transfection of TUC-3 cells with PNC-7 plasmid exhibited the phenotype shown in Panel C of FIG. 3. These cells, which are seen to be enlarged with enlarged nuclei but have distinct cell boundaries, grew only sluggishly to confluence, and strongly resemble viable revertant cells that resulted from the treatment of TUC-3 cells with the anti-protein kinase C inhibitor, CGP 41 251 (16). These cells fail to grow in soft agar (16).

Morphologically Revertant Cells do not Form Tumors in Nude Mice.

To test whether morphologically revertant cells were functionally revertant, $5 \times 10^6$ cells treated for two weeks with 100 ug/ml PNC-2-leader peptide were explanted subcutaneously into each of five nude mice while the same number of untreated TUC-3 cells were concomitantly similarly explanted. The results, shown in Table 4, indicate that morphologically revertant cells fail to form tumors up to two months after reversion while untreated cells form tumors rapidly (within 1 week). At three weeks, all of the nude mice injected with untreated TUC-3 cells were found to have large primary nodules and multiple other nodules and metastatic cancer, with ascites and other sites. Similar results (not shown) to those obtained with PNC-2-leader peptide-treated TUC-3 cells were obtained for morphologically revertant cells resulting from TUC-3 cells treated with PNC-7-leader peptide.

Both PNC-2 and PNC-7 peptides block mitogenic signaling by oncogenic ras-p21 in oocytes but have little effect on signaling by insulin-activated wild-type cellular p21 (5). This finding suggested to us that growth of mammalian cells transformed by oncogenic ras-p21 can be selectively blocked by these peptides without affecting normal growth processes.

Both PNC-2 and PNC-7 peptides induce 100 percent phenotypic reversion of ras-transformed pancreatic (TUC-3) cancer cells and have no apparent effects on the growth of the normal counterpart BMRPA1 cell line. This effect is specific since neither the X13-leader control peptide nor the plasmid encoding it has any effect on TUC-3 cell proliferation. That the PNC-2 and 7 sequences and not the leader sequence, are responsible for this effect is supported by the absence of any effect on TUC-3 cells of the X13-leader peptide and by the finding that the plasmids encoding PNC-2 and PNC-7 without the leader sequence induces the same observed phenotypic reversion.

A surprising finding is that the phenotypic reversion induced by both peptides occurs over a prolonged period of time (120 days), as revealed by the absence of any tumor growth of these cells when explanted into nude mice. Since the half-lives of these peptides is expected to be much shorter than two months, their effects are not likely to be caused by their continuing presence. Significantly, the prolonged reversion effect appears to be independent of the site of action of these peptides since PNC-2 blocks oncogenic ras-p21-JNK interactions (5, 11, 12) while PNC-7 blocks oncogenic ras-p21-raf interactions (14, 15).

It is possible that both peptides activate rapid expression of other proteins that interfere with oncogenic ras-induced cell proliferation. This type of effect has been observed in human pancreatic carcinoma cells induced to revert by the agent azatyrosine that is known to induce expression of the ras recision gene (rrg) (22, 23) and which also selectively blocks oncogenic ras-p21-induced oocyte maturation (13). Another possibility is that each peptide, by blocking signal transduction unique to the oncogenic ras-p21-induced pathway, allows other inhibitory processes continuously to deactivate critical elements in this pathway.

The activity of both PNC-2 and PNC-7 peptides contrasts with that of another oncogenic-ras-p21-specific inhibitor, the staurosporine derivative, CGP 41 251, that selectively inhibits protein kinase C (PKC)(24). This agent blocks oncogenic ras-p21-induced oocyte maturation but has much less effect on insulin-activated wild-type ras-p21-induced maturation (13). In contrast to the results with PNC-2- and 7-leader peptides, this agent induces both necrosis and phenotypic reversion of TUC-3 cells (16) and is cytotoxic to BMRPA1 cells, although surviving cells grow rapidly into stable monolayers (16). Cytotoxicity of CGP 41 251 may be due to its blocking critical PKC-dependent cell processes that may not be involved in cell proliferation.

In prior studies, it had been found that PKC and JNK require each others presence on the oncogenic ras-p21 signal transduction pathway (25). In addition, PNC-2 synergizes with CGP 41 251 in TUC-3 cells in that it significantly lowers its $IC_{50}$ for induction of cytotoxicity to a level that is not toxic to BMRPA1 cells (16). This finding suggests the possibility that PNC-2, which blocks ras-p21-induced activation of JNK (5), inhibits the mutual PKC-JNK activation cycle thereby removing an important activation process, resulting in facilitation of inhibition by CGP 41 251.

Evidently PNC-2 and PNC-7 exert a more selective effect that is specific to the oncogenic ras-p21 pathway, hence the lack of cytotoxicity of these peptides. This finding indicates that these peptides are useful in the treatment of ras-induced human tumors.

TABLE 4

Growth of TUC-3 Cells and Morphologically Reverted TUC-3 Cells Treated with PNC-2 Peptide Explanted into Nude Mice.[a]

| Time (days) | Tumor Nodule Size (mm)[b] | |
| --- | --- | --- |
| | TUC-3 Cells | PNC-2-Treated TUC-3 |
| 0 | 0.0 | 0.0 |
| 7 | 4.8 ± 1.8 | 0.0 |
| 14 | 11.7 ± 2.3 | 0.0 |
| 21 | 14.8 ± 3.6[c] | 0.0 |
| 28 | — | 0.0 |
| 42 | — | 0.0 |
| 56 | — | 0.0 |

[a]An amount of 5 × 10[6] TUC-3 cells was injected into the posterior cervical fat pad of each of 5 nude mice, and the same number of TUC-3 cells treated for 2 weeks with PNC-2-leader peptide was injected into the posterior cervical fat pad of another 5 nude mice.
[b]Expressed as the means ± SD for the five mice in each group.
[c]Multiple nodules and tumor metastasis with ascites occurred in all five mice at this time. Further observations were therefore discontinued.

EXAMPLE III

PNC-2 and PNC-7 Block the Interaction of JNK and MAP Kinase with Val 12-Ras p21 Inside the Cell In these experiments, the Ha-ras form of Val 12-p21 was injected into oocytes (100 ug/ml, 50 nl per oocyte) either alone or together with inhibitory p21 peptide (residues 96-110 shown in this figure). Mature oocytes (non-matured oocytes were used with inhibitory p21 96-110 peptide since it strongly inhibits maturation) were collected after 24 hours (about 50% maturation, approximately 100 oocytes) and subjected to lysis in buffer consisting of 0.35 M LiCl, 50 mM HEPES, pH 7.6, 1 mM EGTA, 1 mM dithiothreitol (DDT), 2 mM MgCl, 50 mM NPP, 1 mM sodium vanadate, and an inhibitor 'cocktail' consisting of 1 µg/ml each of the protease inhibitors: pepstatin, leupeptin and aprotinin; and the phosphatase inhibitors: 1 mM sodium orthovanadate and 5 mM sodium fluoride). The lysate was centrifuged for 15 min at 17000×g at 4° C., and the supernatant was either used directly. The lysates were then subjected to immunoprecipitation using an anti-Ha-ras antibody (CalBiochem). In this procedure, cell lysate was first pre-cleared by incubation with 50 ul of protein A beads for 1 hr at room temperature, followed by centrifugation. Anti-Ha-ras antibody was added to the lysate such that 0.1 ug antibody was added per 250 ug of pre-cleared lysate protein. A volume of 25 µl protein A agarose beads (Sigma) was then added to the incubation mixture, and the resulting mixture was incubated overnight at 4° C., after which the mixture was centrifuged, and the immunoprecipitate was washed three times with 0.5 ml of kinase buffer as described above. Immunoprecipitates were subjected to SDS-PAGE as described above in the preceding paragraph and blotted with anti-Ha-ras (1:2000 with 0.25% BSA), anti-raf (CalBiochem, San Diego, Calif.), diluted 1:2000 with 0.25% BSA, anti-JNK polyclonal antibody (1:2000), anti-MEK (CalBiochem) and anti-MAPK, diluted 1:2000 with 0.25% BSA. All incubations were performed as described in the preceding paragraph, i.e., for 12 hr at 4° C., after which the membranes were washed three times with Tris-buffered saline with Triton (TBS-T) and incubated with anti-rabbit secondary antibody (Pierce, Rockford, Ill.) at 1:20000 dilution. Detection was accomplished using the ECL chemiluminescence detection kit (Pierce). An identical set of experiments was performed with oocytes incubated for 24 h with 10 ug/ml insulin (Sigma, St. Louis, Mo.).

Figure 4A:
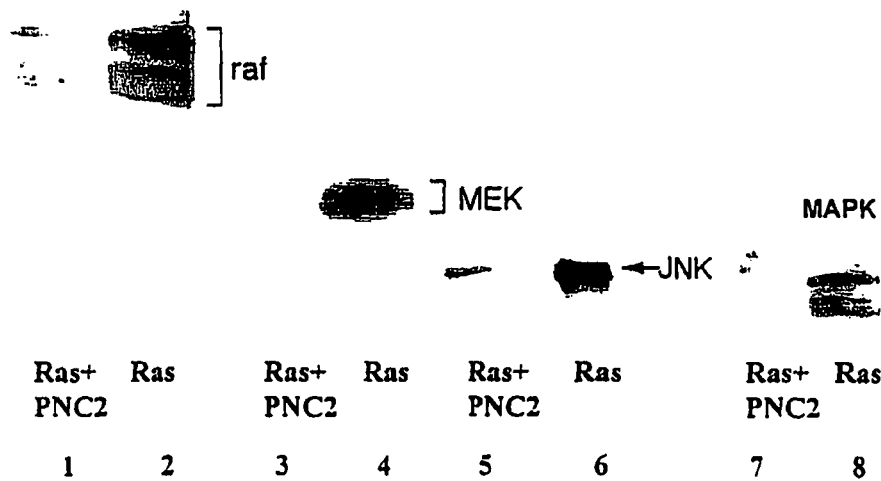
FIG. 4A is a photograph of gel blots showing co-immunoprecipitation of jun-N-terminal kinase (JNK) (lane 6) and MAP kinase (MAPK or ERK) with Ha-ras-p21, immunoprecipitated from oocytes that were induced to maturity by microinjection of oncogenic Val 12-Ha-ras-p21 and blotted.

FIG. 4A shows the results of injected Val 12-p21 forming a complex with raf, MEK, JNK and MAPK (ERK). Oocytes that matured after being injected with Val 12-Ha-ras-p21 were lysed and immunoprecipitated with anti-Ha-ras antibody. The immunoprecipitate was blotted with anti-raf (lane 2), anti-MEK (lane 4), anti-JNK (lane 6) and anti-MAPK (lane 8). Oocytes were also injected with Val 12-p21 and ras-p21 inhibitory peptide 96-110, labeled as PNC-2, lysed and subjected to immunoprecipitation with anti-Ha-ras. These immunoprecipitates were then blotted with anti-raf (lane 1), anti-MEK (lane 3), anti-JNK (lane 5) and anti-MAPK (lane 7). As can be seen in this figure, raf, MEK, JNK and MAPK all co-precipitate with Ha-Val 12-ras-p21. On the other hand, in the presence of the two inhibitory peptides, none of these proteins precipitated with Val 12-ras-p21 although there is still some binding to raf.

Figure 4B:
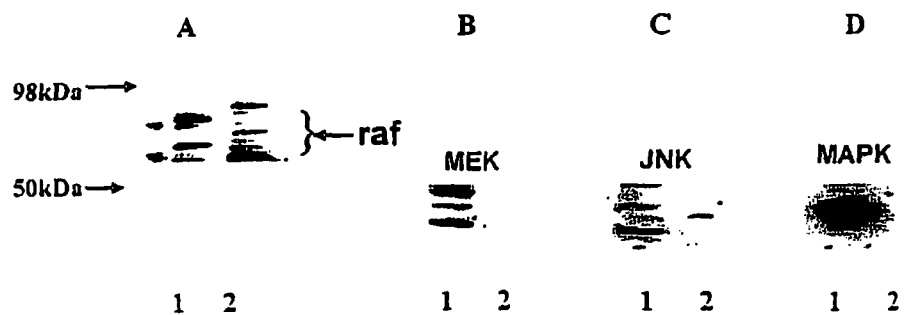
FIG. 4B is a photograph of gel blots showing co-immunoprecipitation of jun-N-terminal kinase (JNK) (lane 6) and MAP kinase (MAPK or ERK) with Ha-ras-p21, immunoprecipitated from oocytes that were induced to maturity with insulin, which activates wild-type rs-p21. Only raf was found to immunoprecipitate with Ha-ras in these oocytes.

The same experiment, the results of which are shown in FIG. 4A was performed on oocytes that were induced to mature with insulin. FIG. 4B shows blots for raf (A), MEK (B), JNK(C) and MAPK (D). The first lane for each of these four sets presents the results for the blots of whole cell lysate to demonstrate the presence of each protein. The second lane in each set of blots shows the results of blotting for each protein in the anti-Ha-ras-p21 immunoprecipitate. As can be seen in this figure, only raf co-precipitates with endogenous Ha-ras-p21 in the oocytes. Thus oncogenic, but not activated wild-type, ras-p21 forms a large complex with vital mitogenic signal transducing proteins and induces activation of raf- MEK-MAP kinase (MAPK or ERK) and JNK-jun pathways while insulin-activated wild-type p21 (at least the Ha-ras form) forms a complex only with raf.

REFERENCES

1. Barbacid, M. (1987) ras Genes. Ann. Rev. Biochem. 56, 779-827.
2. Pincus, M. R., Brandt-Rauf, P. W., Koslosky, W. and Appruzzese, W. (2001) Cell Biology and Early Tumor Detection (Chapter 64) in Henry, J. B., Ed., Clinical Diagnosis and Management by Laboratory Methods, Nineteenth Edition, W. B. Saunders, Philadelphia, 1344-1354.
3. Birchmeier, C., Broek, D., and Wigler, M. (1985) ras proteins can induce meiosis in *Xenopus* oocytes. Cell 43, 615-621.
4. Deshpande, A. K. and Kung, H.- F. (1987) Insulin induction of *Xenopus laevis* oocyte maturation is inhibited by monoclonal antibody against p21 ras proteins. Mol. Cell. Biol. 7, 1285-1288.
5. Pincus, M. R., Brandt-Rauf, P. W., Michl, J. and Friedman, F. K. (2000) ras-p21-Induced Cell Transformation: Unique Signal Transduction Pathways And Implications for the Design of New Chemotherapeutic Agents. Cancer Invest. 18, 39-50.
6. Chen, J. M., Monaco, R., Manolatos, S., Brandt-Rauf, P. W., Friedman, F. K., and Pincus, M. R. (1997) Molecular Dynamics on Complexes of ras-p21 and its Inhibitor Protein, rap-1A, Bound to the ras-Binding Domain of the raf-p74 Protein. Identification of Effector Domains in the raf Protein. J. Protein Chem. 16, 631-635.
7. Chung, D., Amar, S., Glozman, A., Chen, J. M., Friedman, F. K., Robinson, R., Monaco, R., Brandt-Rauf, P. W., Yamaizumi, Z. and Pincus, M. R. (1997) Inhibition of Oncogenic and Activated Wild-Type ras-p21 Protein-Induced Oocyte Maturation by Peptides from the ras Binding Domain of the raf-p74 Protein, Identified from Molecular Dynamics Calculations. J. Protein Chem. 16, 619-629.
8. Chen, J. M., Rijwani, K., Friedman, F. K., Hyde, M. J. and Pincus, M. R. (2000) Identification, Using Molecular Dynamics, of an Effector Domain of the ras-Binding Domain of the raf-p74 Protein That Is Uniquely Involved in Oncogenic ras-p21 Signaling. J. Protein Chem. 7, 543-549.
9. Chen, J. M., Friedman, F. K., Hyde, M. J., Monaco, R. and Pincus, M. R. (2000) Molecular Dynamics Analysis of the Structures of ras-Guanine Nucleotide Exchange Protein (SOS) Bound to Wild-Type and Oncogenic-ras-p21. Identification of Effector Domains of SOS. J. Protein Chem. 18, 867-874.
10. Chie, L., Chen, J. M., Friedman, F. K., Chung, D. L., Amar, S. Michl, J., Yamaizumi, Z. and Pincus, M. R. (2000) Inhibition of Oncogenic and Activated Wild-Type ras-p21 Protein-Induced Peptides from the Guanine-Nucleotide Exchange Protein, SOS, Identified from Molecular Dynamics Calculations. Selective Inhibition of Oncogenic ras-p21. J Protein Chem. 18, 875-879.
11. Adler, V., Pincus, M. R., Brandt-Rauf, P. W. and Pincus, M. R. (1995) Complexes of ras-p21 with jun-N-Kinase and c-jun Proteins. Proc. Natl. Acad. Sci. USA 92, 10585-10589.
12. Adler, V., Pincus, M. R., Polatskaya, A., Montano, X., Friedman, F. K. and Ronai, Z. (1996) Activation of c-jun $NH_2$ Kinase by UV Irradiation Is Dependent on $p21^{ras}$ J. Biol. Chem. 271, 23304-23309.
13. Chung, D. L., Joran, A., Friedman, F. K., Robinson, R. R., Brandt-Rauf, P. W., Weinstein, I. B., Ronai, Z. A., Baskin, L., Dykes, D. C., Murphy, R. B., Nishimura, S. Yamaizumi, Z., and Pincus, M. R. (1992) Evidence that Oocyte Maturation Induced by an Oncogenic ras p21 Protein and Insulin Is Mediated by Overlapping Yet Distinct Mechanisms. Exp. Cell Res. 203, 329-335.
14. Chie, L., Friedman, F. K., Kung, H.- F., Lim, M. C. M., Chung, D. L. and Pincus, M. R. (2002) Identification of the Site of Inhibition of Mitogenic Signaling by Oncogenic ras-p21 by a ras Effector Peptide. J. Protein Chem., in press.
15. Chie, L., Chen, J. M., Friedman, F. K., Chung, D. L., Amar, S. Michl, J., Yamaizumi, Z., Brandt-Rauf, P. W. and Pincus, M. R. (2000) Identification of the Site of Inhibition of Oncogenic ras-p21-Induced Signal Transduction by a Peptide from a ras Effector Domain. J Protein Chem. 18, 881-884.
16. Way, D., Smith, S., Sivendran, S., Kanovsky, M., Brandt-Rauf, P. W., Chung, D. L., Michl, J. and Pincus, M. R. (2002) A Protein Kinase C Inhibitor Induces Phenotypic Reversion of ras-Transformed Pancreatic Cancer Cells and Cooperatively Blocks Tumor Cell Proliferation with an Anti-ras Peptide. Cancer Chemother. Pharmacol., in press.
17. Bao, L. Y., Thelmo, W. L., Somnay, S., Madahar, C. and Michl, J. (1994) Characterization of an Acinar Cell Line, BMRPA.430, Derived from Adult Rat Pancreas. FASEB J. 8, 64A.
18. Almoguerra, C., Shibata, D., Forrester, K., Martin, J., Arnheim, M. and Perucho, M. (1988) Most human carcinomas of the endocrine pancreas contain mutant c-K-ras genes. Cell 53, 813-815.
19. Derossi, D., Chassaing, G., Prochiantz, A. (1998) Trojan Peptides: The Penetratin System for Intracellular Delivery. Trends Cell Biol. 8, 84-87.
20. Kanovsky, M., Raffo, A., Drew, L., Rosal, R., Do, T., Friedman, F. K., Rubinstein, P., Visser, I., Robinson, R., Brandt-Rauf, P. W., Michl, J., Fine, R. L. and Pincus, M. R. (2001) Peptides from the Amino Terminal mdm-2 Binding Domain of p53, Designed from Conformational Analysis, Are Selectively Cytotoxic to Transformed Cells. Proc. Natl. Acad. Sci. USA 98, 12438-12443.
21. Kovac, C., Chie, L., Morin, J., Friedman, F. K., Robinson, R., Chung, D. L., Kanovsky. M., Flom, J., Brandt-Rauf, P. W., Yamaizumi, Z., Michl, J. and Pincus, M. R. (2000) Plasmid Expression of a Peptide that Selectively Blocks Oncogenic ras-p21-Induced Oocyte Maturation. Cancer Chemother. Pharmacol. 45, 441-449.
22. Shindo-Okada, N., Makabe, O., Nagahara, H., and Nishimura, S. (1989) Permanent conversion of mouse and human cells transformed by activated ras or raf genes to apparently normal cells by treatment with the antibiotic azatyrosine. Mol. Carcin. 2, 159-167.
23. Contente, S., Kenyon, K., Rimoldi, D. and Friedman, R. M. (1990) Expression of gene rrg is associated with reversion of NIH 3T3 transformed by LTR-c-H-ras. Science 249, 796-798.
24. Meyer, T., Regenass, U., Fabbro, D. Alteri, E., Rosel, J., Muller, M., Caravatti, G., and Matter, A. (1989) A derivative of staurosporine (CPG 41 251) shows selectivity for protein kinase C inhibition and in vivo anti-tumor activity. Int. J. Cancer 43, 851-856.
25. Chung, D., Villafania, A., Anwar, K., Amar, S., Rijwani, K., Kung, H.- F., Adler, V. Ronai, Z. Brandt-Rauf, P. W., Yamaizumi, Z. and Pincus, M. R. (1998) Mutual Dependence of jun-N-Terminal Kinase and Protein Kinase C on the Oncogenic ras-p21 Protein-Induced Mitogenic Signaling Pathway. Med. Sci. Res. 26, 147-150.

26. Bramson, J. L., Graham, F. L. and Gauldie, J.; Curr. Opin. Biotechnol. 1995, 6: 590-595: The use of adenoviral vectors for gene therapy and gene transfer in vivo.
27. Hitt, M. M., Addison, C. L. and Graham, F. L.; Adv. Pharmacol. 1996, 40: 137-206: Human adenovirus vectors for gene transfer into mammalian cells.
28. Graham F L, Smiley, J., Russel, W. C., and Narin, R. (1977). Characteristics of a Human Cell Line Transform3ed by DNA from Human Adenovirus Type 5. J. Gen. virol. 36, 59-74.
29. Lusky, Christ et al., 1998 "In vitro and in vivo biology of recombinant adenovirus vectors with E1, E1/E2A, or E1/E4 deleted" J. Virol. 72(3):2022-3.
30. O'Neal, Zhou et al., 1998 "Toxicological comparison of E2a-deleted and first-generation adenoviral vectors expressing alpha1-antitrypsin after systemic delivery" Human Gene Therapy 9(11):1597-98.
31. Chen, Mack et al., 1997 "Persistance in muscle of an adenoviral vector that lacks all viral genes" Proc. Natl. Acad. Sci. USA 94(4):1414-1419.
32. Morral, N., R. J. Parks, et al. (1998) "High doses of a helper-dependent adenoviral vector yield supraphysiological levels of alpha 1-antritrypsin with negligible toxicity." Human Gene Therapy 9(18):2709-2716.
33. Morral, O'Neal et al., 1999 "Administration of helper-dependent adenoviral vectors and sequential delivery of different vector serotype for long-term liver-directed gene transfer in baboons." Proc. Natl. Acad. Sci. USA 96(22): 12816-12821.
34. Kozarsky, K F and Wilson J M (1993) Gene Therapy: Adenovirus Vectros. Curr. Opin. Genet. Dev. 3, 499-503.
35. Krougliak V, and Graham F L (1995). Development of Cell Lines Capable of Complementing E1, E4, and Protein IX Defective Adenovirus Type 5 Mutants. Hum. Gene Ther. 6, 1575-1586.
36. Stow, N. D., 1981, "Cloning a DNA fragment from the left-hand terminus of the adenovirus type 2 genome and its use in site-directed mutagenesis" J. Virol. 37:171-180.
37. Crouzet J, L. Naudin et al., 1997, "Recombinational construction in Escherichia coli of infectious adenoviral genomes" Proc. Natl. Acad. Sci. USA 94(4):1414-1419.

What is claimed is:

1. A method of treating a patient suffering from a cancer that expresses oncogenic ras-p21 protein, said method comprising administering to the patient, a therapeutically effective amount of an AdV vector, said AdV vector comprising a promoter sequence operably linked to a nucleotide sequence encoding an isolated peptide, wherein the isolated peptide comprises the amino acid sequence YREQIKRVKDSDDVP (SEQ ID NQ:1).

2. A method of inducing phenotypic reversion of cancerous cells to non-cancerous cells in a subject, wherein said cancerous cells express oncogenic ras-p21 protein, said method comprising administering to the subject, a therapeutically effective amount of an AdV vector, said AdV vector comprising a promoter sequence operably linked to a nucleotide sequence encoding an isolated peptide, wherein the isolated peptide comprises the amino acid sequence YREQIKRVKDSDDVP (SEQ ID NO:1).

3. The method of claim 2 wherein the cancerous cells that express oncogenic ras-p21 protein are colon cancer cells, pancreatic cancer cells, non-small cell carcinoma of the lung, gastric cancer cells, bladder cancer cells or mesothelioma cells.

* * * * *